United States Patent
Comanducci

(10) Patent No.: US 7,691,070 B2
(45) Date of Patent: Apr. 6, 2010

(54) APPARATUS FOR MONITORING THE PRESENCE OF SECRETIONS IN THE RESPIRATORY SYSTEM OF A PATIENT

(75) Inventor: Iacopo Comanducci, Arezzo (IT)

(73) Assignee: Cristina Madrignani, Sarzana (IT), part interest ( * ) Notice: Subject to any disclaimer, the term of this patent is extended or adjusted under 35 U.S.C. 154(b) by 1267 days.

(21) Appl. No.: 10/496,907

(22) PCT Filed: Nov. 12, 2002

(86) PCT No.: PCT/EP02/12612

§ 371 (c)(1),
(2), (4) Date: May 27, 2004

(87) PCT Pub. No.: WO03/045250

PCT Pub. Date: Jun. 5, 2003

(65) Prior Publication Data

US 2005/0043607 A1    Feb. 24, 2005

(30) Foreign Application Priority Data

Nov. 29, 2001    (EP) .................................. 01830733

(51) Int. Cl.
*A61B 5/08*    (2006.01)

(52) U.S. Cl. ............. 600/529; 128/204.23; 128/207.14; 600/484; 600/586

(58) Field of Classification Search .......... 600/529–543
See application file for complete search history.

(56) References Cited

U.S. PATENT DOCUMENTS

| | | | | |
|---|---|---|---|---|
| 3,990,435 A | * | 11/1976 | Murphy | 600/529 |
| 4,383,534 A | * | 5/1983 | Peters | 600/484 |
| 4,607,643 A | * | 8/1986 | Bell et al. | 600/528 |
| 4,917,107 A | | 4/1990 | Bell et al. | |
| 5,056,514 A | * | 10/1991 | DuPont | 128/207.14 |
| 5,165,417 A | * | 11/1992 | Murphy, Jr. | 600/529 |
| 5,191,892 A | * | 3/1993 | Blikken | 600/528 |
| 5,655,518 A | * | 8/1997 | Burden | 128/200.26 |
| 5,666,960 A | | 9/1997 | Fredberg et al. | |
| 6,168,568 B1 | * | 1/2001 | Gavriely | 600/529 |
| 2004/0236241 A1 | * | 11/2004 | Murphy | 600/529 |
| 2006/0243280 A1 | * | 11/2006 | Caro | 128/204.23 |

FOREIGN PATENT DOCUMENTS

EP    0 951 866    10/1999

* cited by examiner

Primary Examiner—Patricia C Mallari
Assistant Examiner—Karen E Toth
(74) Attorney, Agent, or Firm—Pearne & Gordon LLP

(57) ABSTRACT

An apparatus for monitoring the presence of secretions in an artificial respiratory system comprises at least one sensing element (20) to detect waves generated by said secretions and output a main signal (50), representative of at least one main parameter characteristic of the waves; a first processing block (30) connected downstream of said first sensing element (20), is set to input the main signal (50) and to generate a corresponding main output alarm signal (51), in the case in which the main parameter has a greater value than a predetermined threshold value.

38 Claims, 2 Drawing Sheets

APPARATUS FOR MONITORING THE PRESENCE OF SECRETIONS IN THE RESPIRATORY SYSTEM OF A PATIENT

The present invention relates to an apparatus for monitoring the presence of secretions in the respiratory system of a patient.

More particularly, the apparatus in accordance with the present invention is adapted to be used for patients that are provided with respiratory prostheses and/or are artificially ventilated following known ventilation modalities, or assisted in ventilation by oxygen-enriched devices for spontaneous ventilation.

It is known that artificially-ventilated patients (in particular those patients that are under intensive therapy) find it difficult to eliminate secretions from the respiratory tract.

It is therefore necessary that the medical assistance and/or nursing staff should carry out removal of said secretions through a procedure called tracheobronchial aspiration. This procedure consists in inserting a pipe (aspiration tube) into the patient's respiratory tract and in aspirating the secretions therein present, thereby allowing the patient to carry out a correct ventilation.

It is very important for said procedure to be executed only if it is really necessary; in fact, tracheobronchial aspiration also represents a factor of risk do to the occurrence of complications such as hypoxemia, atelectasis, cardiac arrhythmias, traumas of the respiratory tract, bronchial spasm, cough, increase in the intracranial pressure and infections.

Consequently, the medical-nursing staff must pay attention so that procedures of tracheobronchial aspiration are not executed in the absence of important secretion volumes.

On the other hand, it is not possible to neglect patients whose respiratory tract is partly obstructed since the persistence of an excessive amount of secretions at the respiratory tract can involve alterations in the patient's respiratory, cardiovascular and metabolic functions, that reveal themselves by reduction in the arterial oxygen saturation, increase in the respiratory frequency and the respiratory fatigue, appearance of episodes of arterial hypertension, tachycardia, trouble with the acid-base balance, increase in the basal metabolism and still other complications known to specialists.

In the light of the above, it is apparent that identifying the right moment for executing a tracheobronchial aspiration is very critical, taking into consideration the fact that serious complications can be caused either neglecting patients needing treatment, or executing the procedure too often.

The known art provides devices capable of detecting and processing signals relating to lung flows, volumes, pressures, in order to study possible alterations in the lung mechanics and the respiratory work through construction of diagrams. The identification of the presence of secretions in said diagrams however, cannot be easily interpreted and interpretation is not at all specific. Therefore such devices are not able to correctly and univocally associate the alterations of the flow-volume curve with the sure presence of stagnant secretions; in addition said devices cannot be applied in combination with particular auxiliary ventilation apparatus and, above all, in the case of patients that are obliged to make exclusive use of an artificial respiratory tract.

Also known is use of apparatus utilising microphonic transducers to formulate diagnoses relative to lung diseases, mainly as regards pneumology and/or lung physiopathology. For instance, magnitudes relating to the respiratory cycle and spectral components of the lung sounds are employed to monitor and possibly classify lung diseases in a patient.

These microphones are occasionally applied to pre-established areas of the patient's body, such as the thorax for example, and generate signals that, once acquired, are submitted to an analog-digital conversion and a software processing through computerized stations and medical validation. Generally therefore, a very complicated electronics is required for these devices and signals must be processed following particular algorithms 20 to be able to supply useful information concerning a patient.

At all events they are not able to communicate the presence of excessive secretion volumes in the patient's respiratory track to the medical assistance staff and consequently are not able to identify the correct moment at which a tracheobronchial aspiration procedure is to be executed.

Therefore, it is an aim of the present invention to provide an apparatus for monitoring the presence of secretions in the respiratory system of a patient that is artificially ventilated or is provided with respiratory prothesis, which apparatus is able to signal to the nursing staff, the moment at which execution of a tracheobronchial aspiration is really necessary.

It is another aim of the present invention to provide an apparatus for monitoring the presence of secretions in a respiratory system which is characterized by a simple and cheap circuit structure.

It is a further aim of the present invention to provide an apparatus for monitoring the presence of secretions in a respiratory system, capable of detecting different magnitudes indicative of the presence of secretions, so as to compare said magnitudes with each other and carry out a very precise and reliable monitoring.

The foregoing and further aims are substantially achieved by an apparatus for monitoring the presence of secretions in the respiratory system of a patient that is provided with a respiratory prothesis or is artificially ventilated in accordance with the features described in the appended claims.

Further features and advantages will become more apparent from the detailed description of a preferred but not limiting embodiment of an apparatus for monitoring the presence of secretions in the, respiratory system of a patient, shown in the accompanying drawings, in which.

Figure 1:
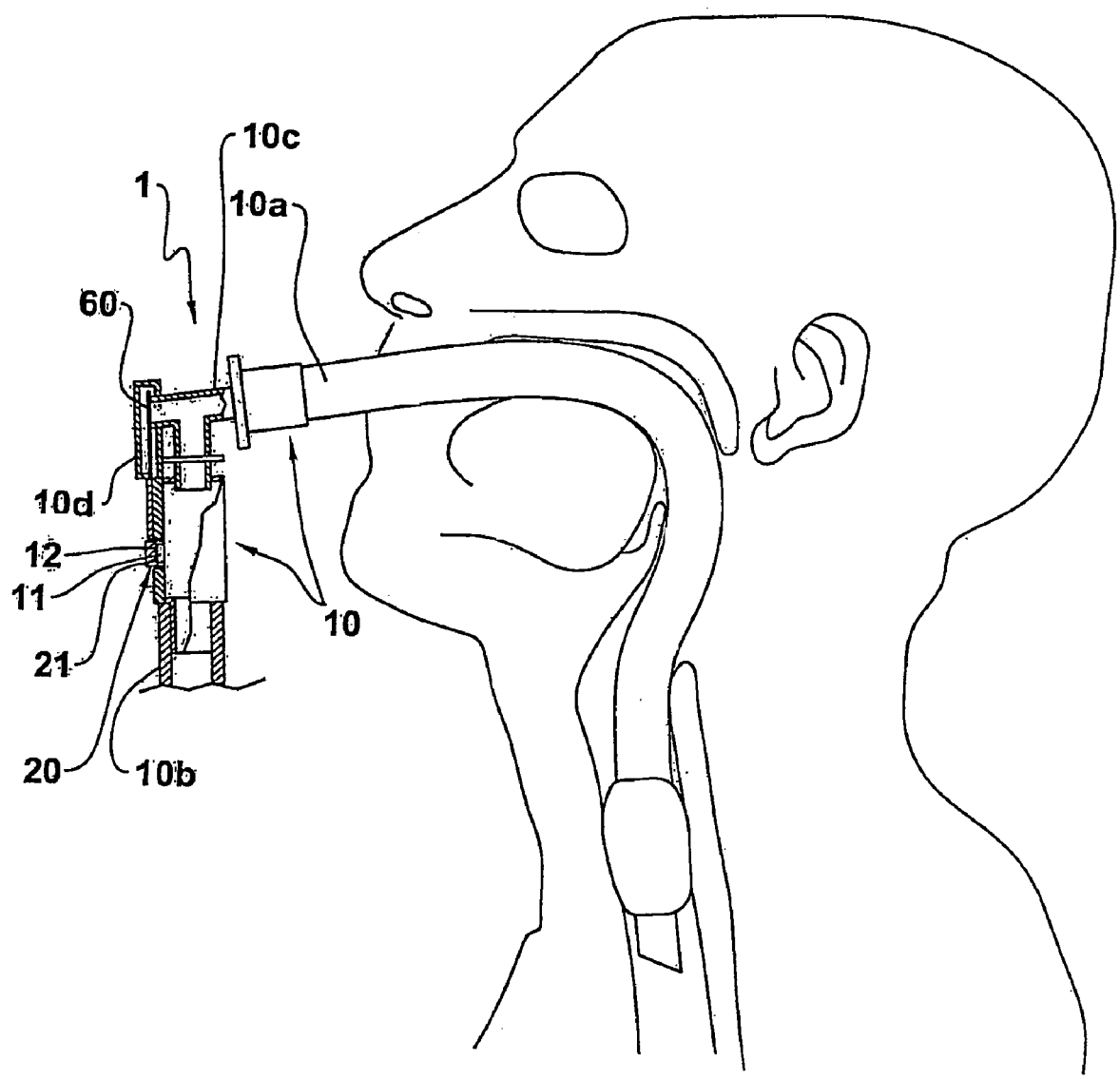
FIG. 1 shows the apparatus of the present invention applied to the orotracheal cavity of an artificially-ventilated patient.

The apparatus for monitoring the presence of secretions in an artificial-ventilation system in accordance with the present invention is generally identified in the figures by reference numeral 1.

Figures 2, 3:
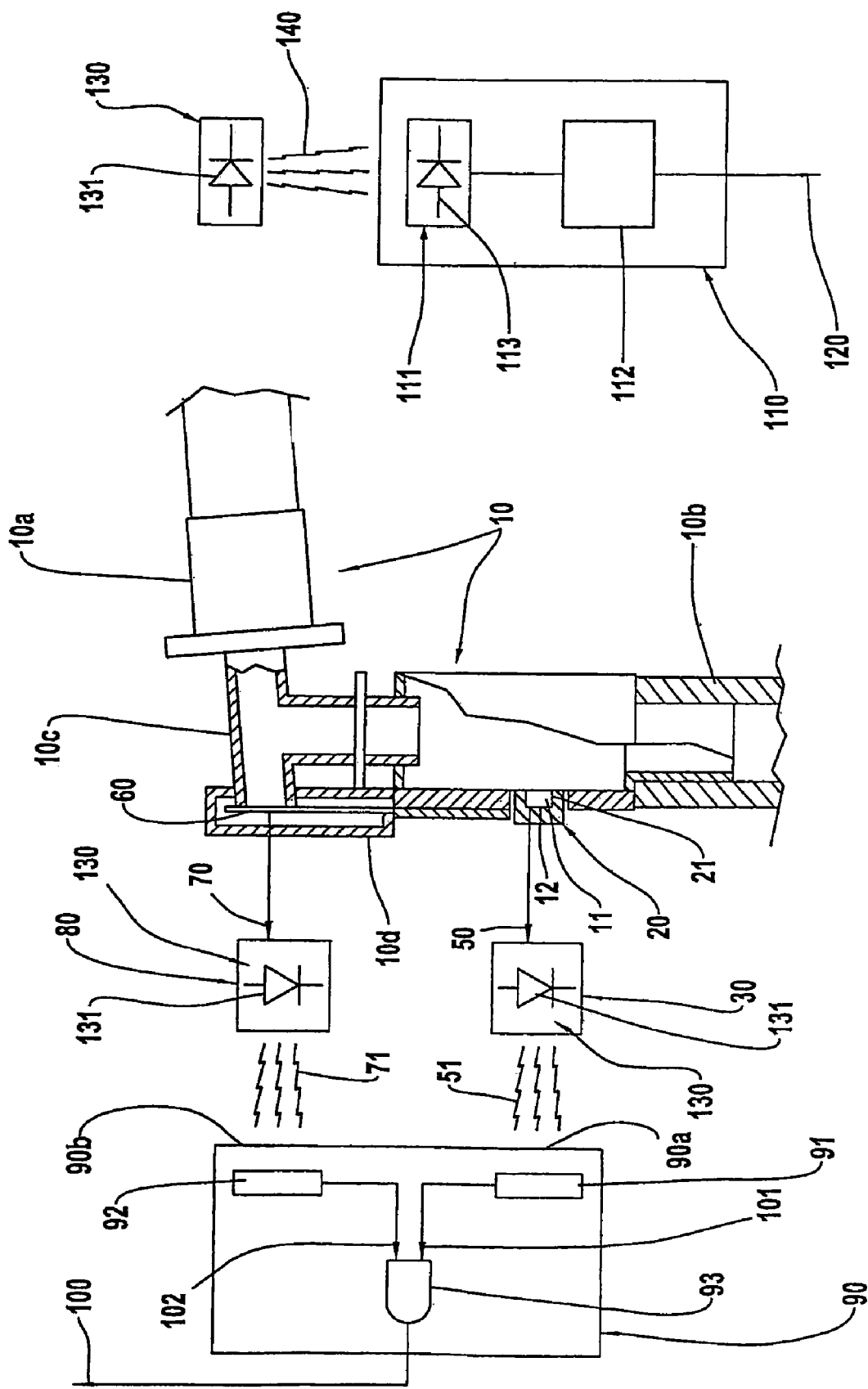
FIG. 2 shows a detail of FIG. 1, together with a block diagram of the circuitry of the apparatus.
FIG. 3 is a block diagram of an auxiliary monitoring circuit of the apparatus.

As can be viewed from FIGS. 1 and 2, apparatus 1 can be associated with an artificial-ventilation system, employed to enable patients with a pulmonary insufficiency to correctly breathe. This system essentially consists of a tubular duct 10 having a first portion 10a insertable in the patient's tracheal cavity, a second portion 10b that is maintained at the outside of the tracheal cavity, and a union element 10c interposed between the first and second portions 10a, 10b.

Through this structure, in combination with appropriate artificial ventilation devices, a patent suffering from respiratory pathologies is allowed a correct respiration.

The apparatus in accordance with the present invention is employed for monitoring the presence of secretions in the patient's respiratory tract; practically, by means of the structure to be described in the following, apparatus 1 is capable of monitoring when the accumulated secretions reach a predetermined volume and of communicating it to the medical and nursing staff.

Referring particularly to FIG. 2, apparatus 1 comprises a first sensing element 20 that is mounted on the tubular duct 10.

The first sensing element 20 is arranged to detect waves generated by the secretions accumulated in the ventilation system and to generate a main output signal 50, representative of at least one main parameter characteristic of these waves. In other words, the main signal 50 incorporates a main parameter, which is selected depending on the processing operations that are to be executed downstream, capable of describing one or more of the physical features of the waves generated by secretions.

These waves may for example comprise acoustic vibrations, propagating into the gasses present in the respiratory system and/or mechanical vibrations, propagating through the patient's natural respiratory tract and the structure of the ventilation circuit, through a side wall 10d of the tubular duct 10 for example.

For reception of vibrations of the acoustic type, the first sensing element 20 comprises an appropriate sound detector 21, conveniently embodied by a microphone of the electret type.

In order to limit noises from other sound or noise sources, the first sensing element 20 can be positioned in a housing 11 defined in a sound-proofing wall 12 of the tubular duct 10 associated, in the example herein shown, with the union element 10c. Alternatively, the sound detector 21 can be mounted on the second portion 10b of the tubular duct 10, or at all events close to the second portion 10b itself.

Alternatively, the first sensing element 20 can be set for detection of mechanical vibrations, generated by secretions and propagating through the side wall 10d of the duct. In this case, the first sensing element 20 comprises an electromechanical transducer, preferably a piezoceramic bimorph transducer, at least partly in engagement by contact with the wall 10d of the tubular duct 10, close to the union element 10c, along either the first portion 10a or the second portion 10b. In this way, the mechanical vibrations generated by secretions can be detected by the first sensing element 20 that also generates the main signal 50 incorporating information relating to said mechanical vibrations.

A first processing block 50 is positioned for connection downstream of said first sensing element 20; it is set to input the main signal 50 and generate a corresponding main output alarm signal 51, should the main parameter have a greater value than a predetermined threshold value.

The main parameter can be advantageously represented by the amplitude of the waves generated by secretions; thus, it is the amplitude of said acoustic and/or mechanical vibrations to be monitored and processed.

In the case of acoustic vibrations, this means that, at the moment the intensity of the sounds generated by the secretions impinged on by respiratory gas flows overcomes a predetermined threshold, the main alarm signal 51 is generated, due to the fact that audio frequencies of some intensity can be only generated by the presence of secretion accumulations of an important volume; consequently at said acoustic vibrations the medical staff is informed about the necessity to carry out removal of the secretions accumulated within the respiratory tract.

On the other hand, in the case of mechanical vibrations, at the moment the oscillation intensity of the secretions is greater than a given limit, the main alarm signal 51 is generated due to the fact that secretion accumulations generate particularly strong mechanical vibrations; it is therefore apparent that if oscillations become strong, tracheobronchial aspiration is required, and the medical nursing staff is immediately warned. The information relating to the main parameter, as above mentioned, is transmitted by the main signal 50, generated by the first sensing element 20.

In a preferred embodiment, it is the amplitude of the main signal 50 that is used to represent the main parameter; in other words, the amplitude of the main signal 50 is a function of said main parameter and, consequently, of the amplitude of the waves generated by secretions.

In particular, the main signal 50 is generated in such a manner that its amplitude is proportional to the main parameter, i.e. to the amplitude of the waves generated by secretions.

A choice of this type is particularly advantageous in order to make the structure of the first processing block 30 as simple as possible, as pointed out in the following.

In fact, generally a comparison between the values taken by the main parameter and the threshold value can be carried out by a circuit structure comprising a memory, set to store said threshold value, and a CPU, capable of comparing the values incorporated in the main signal 50 and the threshold value and generating, if required, the main alarm signal 51.

If the amplitude of the main signal 50, as in the case of the present invention, is proportional to the amplitude of the waves generated by secretions, it is possible to replace the above described circuitry with a filtering element 130 capable of amplitude-filtering the main signal 50 and outputting the main alarm signal 51, should at least one of the spectral components defining the main signal 50 have a greater amplitude than the threshold value.

In other words, this filtering element 130 is able to eliminate all spectral components of the main signal 50 of an amplitude less than the threshold value, whereas the spectral components with an amplitude greater than the threshold value are allowed to pass and are placed at the entrance of the downstream-connected circuit blocks.

In particular, the filtering element 130 may comprise a diode 131, preferably an emitting diode of the LED type. In this case, the main alarm signal 51 can be obtained through the light signal generated by this emitting diode. Consequently, further circuit elements set to generate the main alarm signal 51 are not required to be connected to the filtering element 130.

In fact, the mere visual warning obtained by means of the LED can be sufficient to inform the medical or nursing staff about the fact that a tracheobronchial aspiration is necessary.

To make monitoring carried out by apparatus 1 more reliable, said apparatus can have a combination of the two above described monitoring techniques.

For the purpose, apparatus 1 may be provided with a second sensing element 60 that is associated with the tubular duct 10 and performs the task of detecting the waves generated by the secretions accumulated within the respiratory system.

In particular, by way of example, the second sensing element 60 can be arranged for detection of the mechanical vibrations and operate in combination with the first sensing element 20 of the acoustic type.

In order to detect the mechanical vibrations from secretions, the second sensing element 60 comprises an electromechanical transducer, preferably a piezoceramic bimorph sensor, at least partly positioned in contact with the side wall 10d of the tubular duct 10. The bimorph sensor can be mounted either on the first portion 10a of duct 10, or on the second portion 10b thereof, or also on the union element 10c.

The second sensor 60 is capable of generating an auxiliary output signal 70 incorporating at least one auxiliary parameter characteristic of said waves.

The second sensing element 60 is mounted at the union element 10c of the tubular element 10 and is preferably housed within the union element 10c itself.

A second processing block 80 is positioned for connection downstream of said second sensing element and is set to input the auxiliary signal 70 and generate a corresponding auxiliary output alarm signal 71, should the auxiliary parameter have a greater value than a predetermined threshold value.

Generally the auxiliary parameter represents a physical magnitude characteristic of the waves from secretions; advantageously, the auxiliary parameter may consist of the wave amplitude; thus, it will be the amplitude of said mechanical vibrations to be monitored and processed by the circuitry connected downstream.

In the same manner as above described in relation to the main signal 50, the amplitude of the secondary signal 70 too can be a function of the auxiliary parameter. In particular, the amplitude of the auxiliary signal 70 can be proportional to the auxiliary parameter.

By a signal structured in this way a direct link is created between the amplitude of the mechanical vibrations from the secretions and the amplitude of the auxiliary signal 70 generated by the second sensing element 60.

Since the parameter to be evaluated is the amplitude of the auxiliary signal 70, the second processing block 80 preferably comprises a filtering element 130 capable of amplitude-filtering the auxiliary signal 70; in this manner the spectral components of the auxiliary signal 70 having an amplitude less than the threshold value are eliminated, whereas those with a greater amplitude can be subsequently processed and help in creating the auxiliary alarm signal 71.

In order to make the circuit structure of the second processing block 80 simple and cheap, said filtering element 130 may comprise a diode 131, preferably an emitting diode of the LED type; in this way, the auxiliary alarm signal 71 is directly obtained through the light emission of the LED, so that the responsible staff can be visually warned about the necessity of a tracheobronchial aspiration.

In the light of the above it is apparent that each of the two techniques hitherto described can be also used individually; in other words, apparatus 1 can be provided with a single acoustic sensor or a single detector of mechanical vibrations.

Alternatively, as above mentioned, in order to make signalling more reliable, apparatus 1 may comprise both a first sensor 20 of the acoustic type and a second sensor 60 for detection of mechanical vibrations. In the last-mentioned case, apparatus 1 can be further provided with a combination circuit 90, to receive the main alarm signal 51 and auxiliary alarm signal 71 and generate a corresponding overall alarm signal 100, should said alarm signals 51, 71 be substantially received at the same instant. In this manner, the overall alarm signal 100 is only generated when both the first and second processing blocks 30, 80 signal the presence of an excessive volume of secretions within the respiratory tract; it is apparent that by combining the two monitoring operations in this manner, there is a great increase in the reliability of the final signalling from apparatus 1.

The combination circuit 90 has a first input 90a, associated with the first processing block 30, to receive the main alarm signal 51; in a preferred embodiment, a first photodetector 91 is positioned at the first input 90a, so as to be optically coupled with the emitting diode 131 of the first processing block 30. Upon reception of the main alarm signal 51, the first photodetector 91 outputs a corresponding first transmission signal 101, destined to the downstream-connected circuitry.

The combination circuit 90 further has a second input 90b associated with the second processing block 80, to receive the auxiliary alarm signal 71; in a preferred embodiment, a second photodetector 92 is positioned at the second input 90b so as to be optically coupled with the emitting diode 131 of the second processing block 80. Upon reception of the auxiliary alarm signal 71, the second photodetector 92 outputs a corresponding second transmission signal 102.

The first and second transmission signals 101, 102 are received by a logic circuit 93, preferably embodied by a gate of the AND type, which is set to generate said overall alarm signal 100, in the case of a substantially simultaneous reception of said first and second transmission signals 101, 102.

Practically, the logic circuit 93 performs the task of recognizing the moment at which both the first and second detecting systems signal the presence of excessive secretions in the respiratory tract and ultimately generating the overall alarm signal destined to the nursing stuff.

This overall alarm signal 100 can be a signal either of the acoustic or of the visual type; according to an alternative embodiment, both signalling methods can be used simultaneously.

In order to make monitoring still safer and more reliable, apparatus 1 can also use an IR (infrared) radiation detecting method carried out by an auxiliary monitoring circuit 110, diagrammatically shown in FIG. 3. The last-mentioned technique can be employed in combination with the first one (acoustic detection), the second one (detection of mechanical vibrations) or both of them.

In this case, the emitting diode 131 of the first and/or second processing block 30, 80 is an emitter of IR radiation 140 at a predetermined wavelength, preferably of about 4.2 m.

The first and/or second processing block 30, 80 therefore, instead of generating (main and/or secondary) visible alarm signals, when an excessive volume of secretions is detected, emit an IR radiation 140 passing through the respiratory gases present within the tubular duct 10.

The auxiliary monitoring circuit 110 is provided with a detecting element 111, preferably a photodiode 113 which is coupled with the emitting diode 131 for reception of the IR radiation 140 passed through the gases present in the tubular duct 10.

A signalling circuit 112, connected downstream of the detecting element 111, outputs a warning signal 120 if a reduction in the intensity of the received IR radiation 140 is detected.

In fact, in the presence of volumes of secretions there is a great increase in the concentration of carbon dioxide within the respiratory gases, since secretions give off amounts of $CO_2$. This gives rise to a greater absorption of the IR radiation 140 by the $CO_2$ therein present and, as a result, the intensity of the radiation received by the detecting element 111 is smaller if there is a high concentration of $CO_2$ in the respiratory gases and, consequently, if the volume of the accumulated secretions is of such an amount that a tracheobronchial aspiration is made necessary.

It is apparent that the auxiliary monitoring circuit 110 can be advantageously associated with both the first processing block 30 and the second processing block 80, by associating the detecting element 111 with the logic circuit 93 of the combination circuit 90.

In fact, an IR radiation-emitting diode can be connected downstream of said logic circuit 93 so that the radiation passes through the respiratory gases and is at least partly absorbed by the carbon dioxide present in these gases. Therefore the detecting element 111 is such positioned that it picks up said infrared radiation and enables the signalling circuit 112 to generate the warning signal 120, should the intensity of the received IR radiation decrease to a great extent.

The invention achieves important advantages.

First of all, the apparatus in accordance with the present invention enables the presence of secretions within the patient's respiratory tract to be monitored with great reliability.

In particular, by virtue of the use of one or more of the above described, detection techniques it is possible to avoid the patient being submitted to bronchial aspiration procedures when it is not necessary and, on the other hand, the responsible staff can be timely warned when this procedure is to be really executed.

In addition, the circuit elements herein employed are simple and cheap, since the generated signals are not digitized and therefore no microprocessor is required to be used.

A further advantage is found in the fact that, should visible light-emitting diodes be utilised in the first and/or second processing block, the amplitude of the main signal and/or the auxiliary signal is monitored and the corresponding alarm signal is generated by means of a single circuit element, so that the manufacturing costs and the hardware complexity of the apparatus are minimized.

The invention claimed is:

1. An apparatus for monitoring the presence of secretions in the respiratory system of a patient provided with a respiratory prothesis, having at least one tubular duct consisting of a first portion at least partly insertable in the patient's orotracheal cavity and of a second portion to be positioned externally of the tracheal cavity, further comprising:
   at least one sensing element associated with the tubular duct for detecting waves generated by said secretions and outputting a main signal, representative of at least one main parameter characteristic of said waves, said main signal being defined by one or more spectral components, each having a respective amplitude;
   a processing block, connected downstream of said sensing elements for receiving said main signal as an input and generating a corresponding main output alarm signal, when said main parameter has a value greater than a predetermined threshold value,
   wherein the sensing element is positioned in a housing located in a sound-proofing wall of the tubular duct.

2. An apparatus as claimed in claim 1, wherein said sensing element comprises an acoustic detector, capable of detecting said waves, which waves comprise acoustic vibrations generated by said secretions and propagating through the gases present in said duct.

3. An apparatus as claimed in claim 2, wherein said acoustic detector is a microphone of the electret type.

4. An apparatus as claimed in claim 1, wherein said main parameter consists of the amplitude of said waves.

5. An apparatus as claimed in claim 4, wherein the amplitude of said main signal is a function of said main parameter.

6. An apparatus as claimed in claim 5, wherein the amplitude of said main signal is proportional to said main parameter.

7. An apparatus as claimed in claim 1, wherein said processing block comprises a filtering element capable of amplitude-filtering said main signal and generating the main output alarm signal when at least one of the spectral components of the main signal has a greater amplitude than said threshold value.

8. An apparatus as claimed in claim 1, wherein said tubular duct further comprises a union element interposed between said first and second portions.

9. An apparatus as claimed in claim 1, wherein said sensing element is positioned close to the second portion of the duct.

10. An apparatus as claimed in claim 8, wherein said sensing element is positioned on said union element.

11. An apparatus for monitoring the presence of secretions in the respiratory system of a patient provided with a respiratory prothesis, having at least one tubular duct consisting of a first portion at least partly insertable in the patient's orotracheal cavity and of a second portion to be positioned externally of the tracheal cavity, further comprising:
   a first sensing element associated with the tubular duct for detecting waves generated by said secretions and outputting a main signal, representative of at least one main parameter characteristic of said waves, said main signal being defined by one or more spectral components, each having a respective amplitude;
   a first processing block, connected downstream of said first sensing element, for receiving said main signal as an input and generating a corresponding main output alarm signal, when said main parameter has a value greater than a predetermined threshold value;
   a second sensing element associated with said tubular duct for detecting the waves generated by said secretions and outputting an auxiliary signal that is representative of at least one auxiliary parameter characteristic of said waves, said auxiliary signal being defined by one or more spectral components, each having a respective amplitude;
   a second processing block, connected downstream of said second sensing element for receiving said auxiliary signal as an input and generating an auxiliary output alarm signal, when the auxiliary parameter has a value greater than a predetermined threshold value.

12. An apparatus as claimed in claim 11, wherein said tubular duct further comprises a union element interposed between said first and second portions, said second sensing element being mounted close to the union element of said duct.

13. An apparatus as claimed in claim 11, further comprising a combination circuit having a first input associated with said first processing block, and a second input associated with said second processing block, said combination circuit being set to receive said main and auxiliary alarm signals and to generate a corresponding overall alarm signal when a substantially simultaneous reception of said main and auxiliary alarm signals takes place.

14. An apparatus as claimed in claim 13, wherein each of said first and second processing block comprises a LED type emitting diode, each of said main alarm signal and auxiliary alarm signal being obtained by a light signal generated by said emitting diode, said combination circuit comprising: a first photodetector, positioned at said first input and optically coupled with the emitting diode of the first processing block, said first photodetector being capable of picking up an emission of the main alarm signal and outputting a corresponding first transmission signal; a second photodetector, positioned at said second input and optically coupled with the emitting diode of the second processing block, said second photodetector being capable of picking up an emission of the auxiliary alarm signal and outputting a corresponding second transmission signal; a logic circuit, preferably of the AND gate type, set to input said first and second transmission signals and to generate said overall alarm signal, when a substantially simultaneous reception of said first and second transmission signals takes place.

15. An apparatus as claimed in claim 14, wherein said overall alarm signal is a signal of the optical and/or acoustic type.

16. An apparatus as claimed in claim 11, wherein said first sensing element comprises an acoustic detector, capable of detecting said waves, which waves comprise acoustic vibrations generated by said secretions and propagating through the gases present in said duct.

17. An apparatus as claimed in claim 11, wherein the second sensing element comprises an electromechanical transducer capable of detecting said waves, which waves comprise mechanical vibrations generated by said secretions and propagating through at least one side wall of the tubular duct.

18. An apparatus as claimed in claim 17, wherein said electromechanical transducer is a piezoceramic bimorph sensor positioned at least partly in contact with said side wall.

19. An apparatus as claimed in claim 11, characterized in that said auxiliary parameter consists of the amplitude of said waves.

20. An apparatus as claimed in claim 19, wherein the amplitude of said auxiliary signal is a function of said main parameter.

21. An apparatus as claimed in claim 19, wherein the amplitude of said auxiliary signal is proportional to said auxiliary parameter.

22. An apparatus as claimed in claim 11, wherein said first processing block comprises a filtering element capable of amplitude-filtering said main signal and generating the main output alarm signal when at least one of the spectral components of the main signal has a greater amplitude than said threshold value.

23. An apparatus as claimed in claim 11, wherein said second processing block comprises a filtering element capable of amplitude-filtering said auxiliary signal and generating the auxiliary output alarm signal in the case in which at least one of the spectral components of the auxiliary signal has a greater amplitude than said threshold value.

24. An apparatus as claimed in claim 23, wherein said filtering element comprises a diode.

25. An apparatus as claimed in claim 24, wherein said diode is a LED type emitting diode, said auxiliary alarm signal being obtained by a light signal generated by said emitting diode.

26. An apparatus as claimed in claim 12, wherein said first sensing element is positioned on said union element.

27. An apparatus as claimed in claim 12, wherein said second sensing element is housed within said union element.

28. An apparatus as claimed in claim 23, wherein said filtering element comprises an infrared radiation emitter, said apparatus further comprising at least an auxiliary monitoring circuit provided with: a detecting element coupled with the emitting diode and set to receive the infrared radiation from said emitting diode; a signalling circuit connected downstream of said detecting element and capable of outputting a warning signal on the occurrence of a reduction in the intensity of the infrared radiation received.

29. An apparatus as claimed in claim 28, wherein said detecting element is a photodiode coupled with said emitting diode.

30. An apparatus for monitoring the presence of secretions in the respiratory system of a patient provided with a respiratory prothesis, having at least one tubular duct consisting of a first portion at least partly insertable in the patient's orotracheal cavity and of a second portion to be positioned externally of the tracheal cavity, further comprising:

at least one sensing element associated with the tubular duct for detecting waves generated by said secretions and outputting a main signal, representative of at least one main parameter characteristic of said waves, said main signal being defined by one or more spectral components, each having a respective amplitude;

a processing block, connected downstream of said sensing element for receiving said main signal as an input and generating a corresponding main output alarm signal, when said main parameter has a value greater than a predetermined threshold value, wherein said processing block comprises a filtering element capable of amplitude-filtering said main signal and generating the main output alarm signal when at least one of the spectral components of the main signal has a greater amplitude than said threshold value, wherein said filtering element comprises a diode.

31. An apparatus as claimed in claim 30, wherein said diode is a LED type emitting diode, said main alarm signal being obtained by a light signal generated by said emitting diode.

32. An apparatus as claimed in claim 30, wherein said filtering element comprises an infrared radiation emitter having an emitting diode, said apparatus further comprising at least an auxiliary monitoring circuit provided with:

a detecting element coupled with the emitting diode and set to receive the infrared radiation from said emitting diode;

a signalling circuit connected downstream of said detecting element and capable of outputting a warning signal on the occurrence of a reduction in the intensity of the infrared radiation received.

33. An apparatus as claimed in claim 32, wherein said detecting element is a photodiode coupled with said emitting diode.

34. An apparatus for monitoring the presence of secretions in the respiratory system of a patient provided with a respiratory prothesis, having at least one tubular duct consisting of a first portion at least partly insertable in the patient's orotracheal cavity and of a second portion to be positioned externally of the tracheal cavity, further comprising:

at least one sensing element associated with the tubular duct for detecting waves generated by said secretions and outputting a main signal, representative of at least one main parameter characteristic of said waves, said main signal being defined by one or more spectral components, each having a respective amplitude;

a processing block, connected downstream of said sensing element, for receiving said main signal as an input and generating a corresponding main output alarm signal, when said main parameter has a value greater than a predetermined threshold value, wherein the sensing element comprises an electromechanical transducer capable of detecting said waves, which waves comprise mechanical vibrations generated by said secretions and propagating through at least one side wall of the tubular duct, wherein said electromechanical transducer is a piezoceramic bimorph sensor positioned at least partly in contact with said side wall.

35. An apparatus as claimed in claim 34, wherein said processing block comprises a filtering element capable of amplitude-filtering said main signal and generating the main output alarm signal when at least one of the spectral components of the main signal has a greater amplitude than said threshold value.

36. An apparatus as claimed in claim 34, wherein said tubular duct further comprises a union element interposed between said first and second portions.

37. An apparatus as claimed in claim 36, wherein said first sensing element is positioned on said union element.

38. An apparatus for monitoring the presence of secretions in the respiratory system of a patient provided with a respiratory prothesis, having at least one tubular duct consisting of a first portion at least partly insertable in the patient's orotracheal cavity and of a second portion to be positioned externally of the tracheal cavity, further comprising:

at least one sensing element associated with the tubular duct for detecting waves generated by said secretions and outputting a main signal, representative of at least one main parameter characteristic of said waves, said main signal being defined by one or more spectral components, each having a respective amplitude;

a processing block, connected downstream of said sensing element for receiving said main signal as an input and generating a corresponding main output alarm signal, when said main parameter has a value greater than a predetermined threshold value;

wherein said tubular duct further comprises a union element interposed between said first and second portions, wherein said sensing element is positioned on said union element.

* * * * *